(12) United States Patent  (10) Patent No.: US 7,980,696 B1
Taki et al.  (45) Date of Patent: Jul. 19, 2011

(54) OPHTHALMIC PHOTOGRAPHING APPARATUS

(75) Inventors: Seiji Taki, Aichi (JP); Yukio Abe, Aichi (JP); Hiroyoshi Nakanishi, Aichi (JP); Toshio Murata, Aichi (JP); Yasuhiro Furuuchi, Aichi (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 13/009,940

(22) Filed: Jan. 20, 2011

(30) Foreign Application Priority Data

Jan. 21, 2010 (JP) .................. 2010-011355
Jan. 21, 2010 (JP) .................. 2010-011366

(51) Int. Cl.
*A61B 3/14* (2006.01)
*A61B 3/10* (2006.01)
(52) U.S. Cl. .................. 351/206; 351/205; 351/221
(58) Field of Classification Search .................. 351/200, 351/205, 206, 208, 211, 221
See application file for complete search history.

(56) References Cited

U.S. PATENT DOCUMENTS

| 7,510,282 | B2 | 3/2009 | Ueno et al. |
| 2010/0014089 | A1 | 1/2010 | Yamada et al. |

FOREIGN PATENT DOCUMENTS

| JP | 2008029467 A | 2/2008 |
| JP | 2010012111 A | 1/2010 |

*Primary Examiner* — Jack Dinh
(74) *Attorney, Agent, or Firm* — Lowe Hauptman Ham & Berner LLP

(57) ABSTRACT

An ophthalmic photographing apparatus includes: an interference optical system including a splitter that splits light, emitted from a measurement light source, into measurement light and reference light, and synthesizing the measurement light reflected on an eye with the reference light to guide the synthesized light to a detector; a driving part that moves an optical member arranged in the optical path to adjust an optical-path difference between the measurement light and the reference light; an image obtaining part that obtains a tomographic image of a fundus or an anterior segment based on a light receiving signal output from the detector; and a driving control unit that controls driving of the driving part to locate the optical member in a predetermined position corresponding to either a photographing mode for photographing the tomographic image of the fundus or a photographing mode for photographing the tomographic image of the anterior segment.

14 Claims, 6 Drawing Sheets

OPHTHALMIC PHOTOGRAPHING APPARATUS

CROSS-REFERENCE TO RELATED APPLICATION

This application is based on Japanese Patent Applications No. 2010-011355 and No. 2010-011366 filed with the Japan Patent Office on Jan. 21, 2010, the entire content of which is hereby incorporated by reference.

BACKGROUND

1. Technical Field

An aspect of the present invention relates to an ophthalmic photographing apparatus for photographing a tomographic image of an examinee's eye.

2. Related Art

There is known an ophthalmic photographing apparatus (Optical Coherence Tomography: OCT) which has an interference optical system and photographs a tomographic image of a fundus. The interference optical system of this apparatus splits light emitted from a light source into measurement light and reference light. This interference optical system then guides the measurement light to a predetermined region of an examinee's eye, while guiding the reference light to a reference optical system. Subsequently, the interference optical system synthesizes the measurement light, reflected on the predetermined region of the examinee's eye, with the reference light, to obtain interference light, and thereafter makes a light receiving device receive this interference light. In such an apparatus, an optical member for changing an optical path length is moved in an optical-axis direction. This can adjust an optical-path difference between the measurement light and the reference light in accordance with a difference in ocular axial length (refer to JP-A-2008-29467).

Incidentally, in such an apparatus as described above, an adaptor having a lens system for moving a focal position of the measurement light from the fundus to an anterior segment can be mounted in an inspection window, thereby to also photograph a tomographic image of the anterior segment.

SUMMARY

In the case of intending to photograph the anterior-segment tomographic image in such an apparatus as described above, it is necessary to adjust the optical-path difference between the measurement light and the reference light so as to obtain the anterior-segment tomographic image. However, there have been possibilities that a tomographic image in a state out of focus is obtained, or the lens system of the adaptor is erroneously obtained as a tomographic image. This is considered to be because the tomographic image has been searched by moving the foregoing optical member in a movement range similar to that at the time of photographing the fundus.

A technical object of an aspect of the present invention is to provide an ophthalmic photographing apparatus capable of obtaining a tomographic image of a fundus and a tomographic image of an anterior segment, wherein the anterior-segment tomographic image can be favorably photographed.

The aspect of the present invention includes the following configuration.

An ophthalmic photographing apparatus for photographing a tomographic image of an eye, including:
an interference optical system including:
a measurement light source; and
a splitter that splits light emitted from the measurement light source, such that the split lights travel in a measurement optical path for guiding part of the light to the eye as measurement light and in a reference optical path for generating reference light,
the interference optical system synthesizing reflected light from the measurement optical path, which is obtained by reflection of the measurement light on the eye, with the reference light from the reference optical path, to guide the synthesized light to a detector;
a first driving part that moves an optical member arranged in one of the measurement optical path and the reference optical path in an optical-axis direction in order to adjust an optical-path difference between the measurement optical path and the reference optical path;
an image obtaining part that is connected to the detector and obtains a tomographic image of a fundus in a fundus photographing mode and a tomographic image of an anterior segment in an anterior segment photographing mode based on a light receiving signal output from the detector; and
a driving control unit that controls driving of the first driving part in the case of the fundus photographing mode and driving of the first driving part to locate the optical member in a predetermined position corresponding to the anterior segment photographing mode in the case of the anterior segment photographing mode.

In the ophthalmic photographing apparatus capable of obtaining the tomographic image of the fundus and the tomographic image of the anterior segment, it is possible to favorably photograph the anterior-segment tomographic image.

BRIEF DESCRIPTION OF THE DRAWINGS

The foregoing and other objects, features, aspects and advantages of the invention will become more apparent from the following detailed description when taken in conjunction with the accompanying drawings, in which.

DESCRIPTION OF EMBODIMENTS

Figure 1:
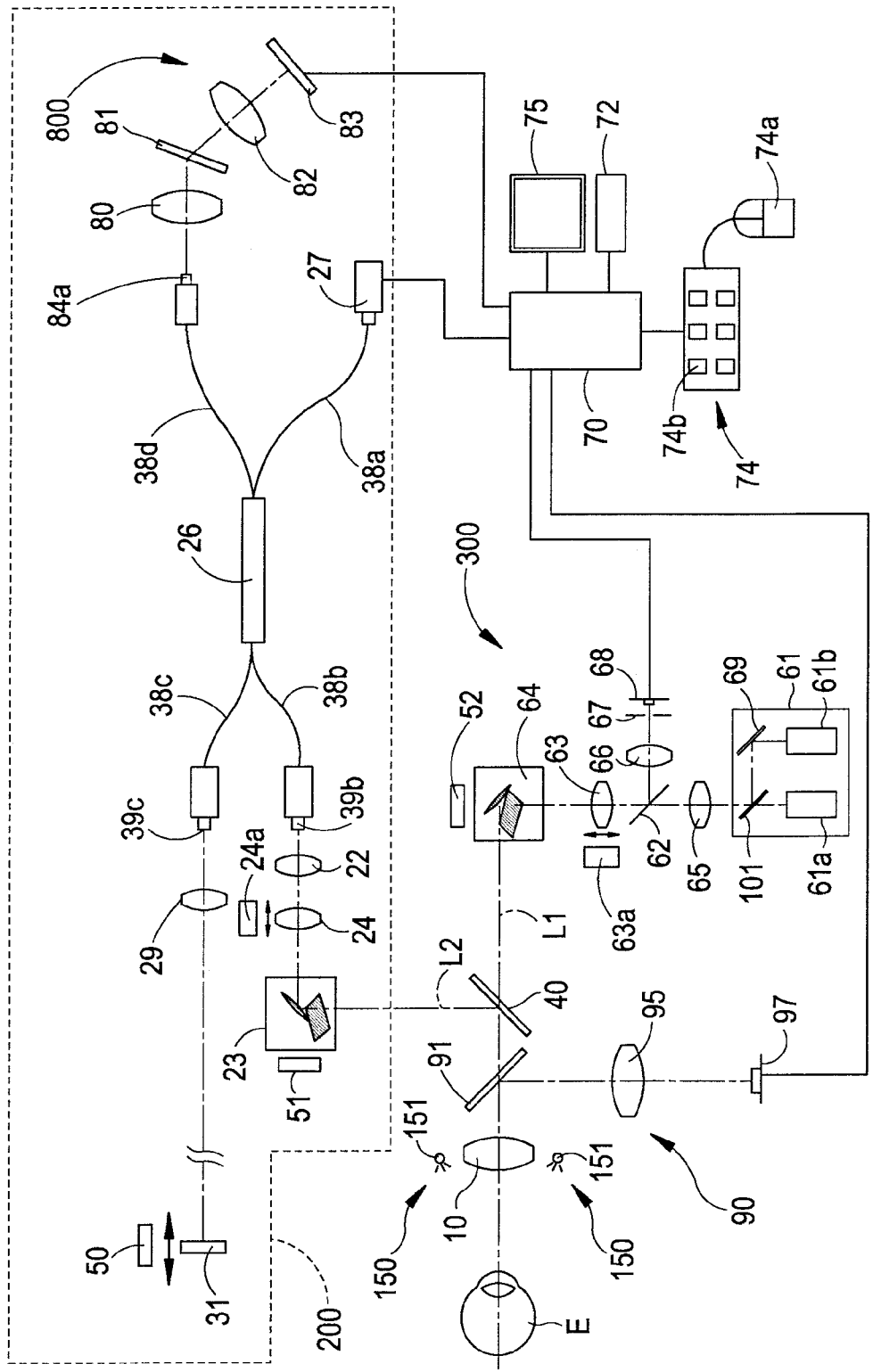
FIG. 1 is a view showing an optical system and a control system of an ophthalmic photographing apparatus of a present embodiment.

Preferred embodiments of the present invention will be described below with reference to the accompanying drawings, in which like reference characters designate similar or identical parts throughout the several views thereof.

An embodiment in accordance with an aspect of the present invention will be described based on the drawings. FIG. 1 is a view showing an optical system and a control system in an ophthalmic photographing apparatus of the present embodiment. It is to be noted that in the present embodiment, a description is given with a depth direction of an examinee's eye referred to as a Z-direction (direction of optical axis L1), a horizontal direction referred to as an X-direction, and a vertical direction referred to as a Y-direction.

As shown in FIG. 1, the optical system of this ophthalmic photographing apparatus is broadly divided into an interference optical system (hereinafter referred to as OCT optical system) 200 and a scanning laser ophthalmoscope (SLO) optical system 300. The OCT optical system 200 serves to obtain a tomographic image of a fundus of an examinee's eye E by use of an optical interference technique. Meanwhile, the SLO optical system 300 illuminates the fundus by use of infrared light, to obtain an SLO fundus image for observing the fundus. It is to be noted that each of the above optical systems has a light projecting optical system and a light receiving optical system, and is used as a photographing optical system for obtaining a photographed image of the eye. The light projecting optical system projects at least part of light emitted from a light source to a predetermined region of the eye. The photographing optical system receives reflected light from the predetermined region of the eye in a light receiving device.

Figure 2A:
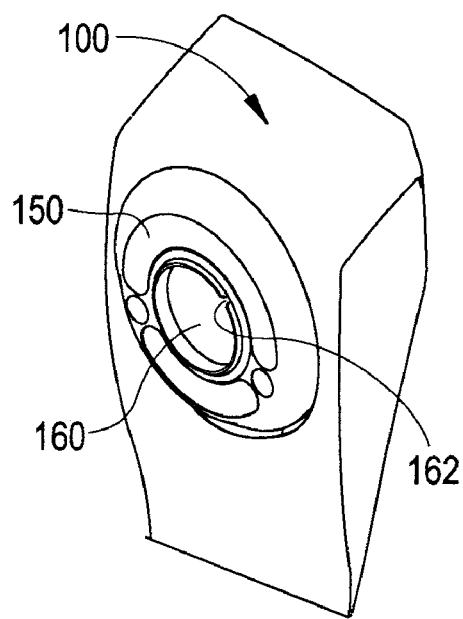
FIGS. 2A and 2B are external perspective views respectively showing the states of the vicinity of an inspection window at the time of not mounting an adaptor and at the time of mounting the same.

As the OCT optical system 200, there has been used an OCT optical system of a spectral domain type. Naturally, a time domain type (TD-OCT) or a swept source domain type (SS-OCT) may also be used. It is to be noted that the OCT optical system 200 and the SLO optical system 300 are incorporated in a housing 100 (refer to FIGS. 2A and 2B). Further, this housing 100 is three-dimensionally moved with respect to the eye E by a known (manual or electrically-powered) movement mechanism for alignment.

It is to be noted that a dichroic mirror 40 is used as a light splitting member. The dichroic mirror 40 has a characteristic of reflecting measurement light (e.g., λ=about 840 nm) emitted from a measurement light source 27 provided in the OCT optical system 200, while being transmitted by laser light (light with a different wavelength from that of the light source 27, e.g., λ=about 780 nm) emitted from a light emitting part 61 provided in the SLO optical system 300. The dichroic mirror 40 makes a measurement optical axis L2 of the OCT optical system 200 and a measurement optical axis L1 of the SLO optical system 300 be the same axial.

A configuration of the OCT optical system 200 provided on the opposite side to the dichroic mirror 40 will be described. The OCT optical system 200 splits a light flux emitted from the light source into a measurement light flux and a reference light flux. Further, the OCT optical system 200 guides the measurement light flux to a predetermined region of the eye (anterior segment or fundus), while guiding the reference light flux to the reference optical system. Subsequently, the OCT optical system 200 makes the light receiving device receive interference light obtained by synthesizing the measurement light flux, reflected on the predetermined region of the eye, with the reference light flux.

The OCT light source 27 emits low coherent light. As the OCT light source 27, there is for example used a light source that emits light with a central wavelength of 840 nm and a band width of 50 nm (e.g., SLD light source). A fiber coupler 26 serves as a light splitting member as well as a light coupling member. The light emitted from the OCT light source 27 passes through an optical fiber 38*a* as a guiding optical path, and is thereafter split by the coupler 26 into reference light and measurement light. The measurement light travels toward the eye E via an optical fiber 38*b*, while the reference light travels toward a reference mirror 31 via an optical fiber 38*c*.

In an optical path for emitting the measurement light toward the eye E, an end 39*b* of the optical fiber 38*b*, a collimator lens 22, a focusing lens 24 and a scanning part 23 are arranged. The focusing lens 24 is movable in the optical-axis direction in line with a refraction error of the eye E for adjustment of a focus on the fundus. The scanning part 23 is capable of scanning the fundus in XY directions with the measurement light. This scanning part 23 includes two galvanometer mirrors, and is operated by driving of a scanning driving mechanism 51. The dichroic mirror 40 and an objective lens 10 serve as a light guiding optical system for guiding OCT measurement light from the OCT optical system 200 to the fundus. It is to be noted that the scanning part 23 of the present embodiment arbitrarily adjusts a reflection angle of the measurement light by means of the two galvanometer mirrors. Hence a direction of scanning by means of the measurement light on the fundus is arbitrarily set. A tomographic image in an arbitrary area of the fundus is thus obtained. It is to be noted that the end 39*b* of the optical fiber 38*b* is arranged in a position conjugate with the fundus of the eye E. Further, the two galvanometer mirrors of the scanning part 23 are arranged in a position substantially conjugate with a pupil of the eye E.

The galvanometer mirrors and the scanning driving mechanism 51 described above are used as an optical scanner (optical scanning part). The optical scanner is arranged in the optical path for the measurement light flux (measurement optical path). The optical scanner changes a traveling direction of the measurement light flux in order to scan the predetermined region of the eye in a transverse direction (XY directions) with the measurement light flux. As the optical scanner, other than the mirror, an acousto-optic device (AOM: Acousto-Optic Modulator) for changing a traveling (deflection) direction of light, and the like are used.

The measurement light emitted from the end 39*b* of the optical fiber 38*b* is collimated by the collimator lens 22, and thereafter reaches the scanning part 23 via the focusing lens 24. In this scanning part 23, the two galvanometer mirrors are driven, to change a reflecting direction of the measurement light. The measurement light reflected on the scanning part 23 is reflected on the dichroic mirror 40, and thereafter collected in the fundus via a dichroic mirror 91 and the objective lens 10.

The measurement light reflected on the fundus passes through the objective lens 10 and the dichroic mirror 91, and is thereafter reflected on the dichroic mirror 40, to travel toward the OCT optical system 200. Further, the measurement light is incident on the end 39*b* of the optical fiber 38*b* via the two galvanometer mirrors of the scanning part 23, the focusing lens 24 and the collimator lens 22. The measurement light incident on the end 39*b* reaches an end 84*a* of an optical fiber 38*d* via the optical fiber 38*b*, the fiber coupler 26 and the optical fiber 38*d*.

Meanwhile, in an optical path for emitting reference light toward the reference mirror 31 (reference optical path), an end 39*c* of the optical fiber 38*c*, a collimator lens 29 and the reference mirror 31 are arranged. The reference mirror 31 is configured to be movable in the optical-axis direction by a reference mirror driving mechanism 50. This allows the reference mirror 31 to change an optical path length of the reference light.

The reference light emitted from the end 39c of the optical fiber 38c is made to be a parallel light flux by the collimator lens 29 and reflected on the reference mirror 31, and is thereafter collected by the collimator lens 29, to be incident on the end 39c of the optical fiber 38c. The reference light incident on the end 39c reaches the coupler 26 via the optical fiber 38c.

The reference light generated as described above and the fundus reflected light obtained by reflection of the measurement light on the fundus are synthesized in the coupler 26, to become interference light. The interference light is emitted from the end 84a through the optical fiber 38d.

A spectroscopic optical system 800 (spectrometer part) splits the interference light into each frequency component for obtaining an interference signal with reference to each frequency. The spectroscopic optical system 800 has a collimator lens 80, a grating (diffraction grating) 81, a condenser lens 82 and a light receiving device (detector) 83. The light receiving device 83 includes a one-dimensional device (line sensor) having the sensitivity to light with a wavelength in an infrared region.

The light emitted from the end 84a is made to be parallel light in the collimator lens 80, and thereafter split in the grating 81 into each frequency component (each wavelength component). The split light is then collected on the light receiving surface of the light receiving device 83 via the condenser lens 82. Thereby, spectrum information with interference fringes is recorded in the light receiving device 83. The spectrum information (light receiving signal) is then input into a control part 70. The control part 70 can analyze the spectrum information by use of Fourier transformation, to measure information (A-scan signal) in the depth direction of the eye. Using the scanning part 23, the control part 70 can scan the fundus in a predetermined transverse direction with the measurement light, to obtain a tomographic image. For example, the control part 70 can scan the fundus in the X-direction or the Y-direction with the measurement light, to obtain a tomographic image in an X-Z plane or a Y-Z plane (it is to be noted that in the present embodiment, such a method for one-dimensionally scanning the fundus with the measurement light to obtain a tomographic image is referred to as B-scan). In addition, the obtained tomographic image is stored in a memory 72 connected to the control part 70. Further, the control part 70 can two-dimensionally scan the fundus in the XY directions with the measurement light, to obtain a three-dimensional image of the fundus.

Next, the SLO optical system (confocal optical system) 300 arranged in a transmitting direction of the dichroic mirror 40 will be described. The SLO optical system 300 is broadly divided into an illuminating optical system for illuminating the fundus and a light receiving optical system for receiving, with the light receiving device, reflected light from the fundus illuminated by the illuminating optical system. The SLO optical system 300 obtains a front image of the fundus based on a light receiving signal output from the light receiving device.

The light emitting part 61 has a first light source (SLO light source) 61a, a second light source (fixation optical system) 61b, a mirror 69, and a dichroic mirror 101. The first light source 61a emits light with a wavelength in the infrared region (e.g., $\lambda$=780 nm), and the second light source 61b emits light with a wavelength in a visible region (e.g., $\lambda$=630 nm). It is to be noted that as the first light source 61a and the second light source 61b, a light source is used which emits light with high luminance and high directivity (such as a laser diode light source or an SLD light source). Infrared light emitted from the first light source 61a passes through the dichroic mirror 101, and travels to a beam splitter 62 through a collimator lens 65. Visible light emitted from the second light source 61b is bent by the mirror 69, and thereafter reflected on the dichroic minor 101. This visible light then travels along the same axis as that of the infrared light emitted from the first light source 61a. The first light source 61a is used for obtaining a fundus front image for observation. Meanwhile, the second light source 61b is used for guiding the sight direction of the eye.

In the optical path for emitting laser light from the light emitting part 61 toward the eye E, the collimator lens 65, a focusing lens 63, the scanning part (optical scanner) 64 and the objective lens 10 are arranged. The focusing lens 63 is movable in the optical-axis direction in line with a refraction error of the eye. The scanning part 64 can perform high-speed scanning on the fundus in the XY directions with the measurement light. The scanning part 64 has a galvanometer mirror and a polygon mirror, and is driven by a scanning driving mechanism 52. Reflected surfaces of the galvanometer mirror and the polygon mirror can be arranged in a position substantially conjugate with the pupil of the eye E.

Further, the beam splitter 62 is arranged between the light emitting part 61 and the focusing lens 63. Moreover, on the reflecting direction of the beam splitter 62, a condenser lens 66, a confocal opening 67 and a light receiving device 68 for SLO are provided. The condenser lens 66 serves to configure the confocal optical system. The confocal opening 67 is arranged in a position conjugate with the fundus.

Herein, laser light (measurement light or fixation light) emitted from the light emitting part 61 transmits the beam splitter 62 via the collimator lens 65, and thereafter passes through the focusing lens 63. Subsequently, this laser light reaches the scanning part 64. By driving of the galvanometer mirror and the polygon mirror, the reflecting direction of this laser light is changed. The reflected laser light transmits the dichroic mirror 40, and is thereafter collected in the fundus via the dichroic minor 91 and the objective lens 10.

The laser light (measurement light) reflected on the fundus passes through the objective lens 10, the dichroic mirror 91, the galvanometer mirror and the polygon mirror of the scanning part 64 and the focusing lens 63, and is then reflected on the beam splitter 62. Subsequently, this laser light is collected in the condenser lens 66, and thereafter detected by the light receiving device 68 via the confocal opening 67. A light receiving signal generated in the light receiving device 68 is input into the control part 70. The control part 70 obtains the front image of the fundus based on the light receiving signal obtained in the light receiving device 68. The obtained front image is stored in the memory 72. It is to be noted that at the time of obtaining the front image (SLO image), scanning (sub-scanning) of laser light in a longitudinal direction by means of the galvanometer mirror provided in the scanning part 64 and scanning (main scanning) of laser light in a transverse direction by means of the polygon mirror are implemented.

<Alignment Target Projecting Optical System>

Further, the ophthalmic photographing apparatus of the present embodiment has a projecting optical system 150 for projecting an alignment target to the eye E. This projecting optical system 150 has an infrared light source 151, and is also arranged outside an inspection window (observation window) 160 provided in the apparatus housing 100. Further, this projecting optical system 150 projects the target diagonally from the front of the eye E (the outside of the objective lens 10 in the radial direction) (refer to external view of a main part of FIG. 2A).

In this projecting optical system 150, for example, a plurality of infrared light sources 151 are concentrically arranged at an interval of 45 degrees with the photographing optical axis L1 at the center. It is to be noted that for the sake of simplicity, FIG. 1 illustrates the infrared light sources 151 arranged in symmetric positions with the photographing optical axis L1 at the center (positions corresponding to 0 degree and 180 degrees).

When an adaptor 500 (refer to FIG. 2B) is not mounted, the infrared light source 151 emits a light flux in the oblique direction toward the anterior segment of the eye E. Upon emission of the infrared light from each infrared light source 151, a raster arranged in ring shape is formed in the anterior segment of the eye E. The projected target image is displayed on a monitor 75 along with the anterior-segment image. This target image is used by an examiner in performing alignment on the eye E. Further, the projecting optical system 150 is used as an anterior-segment illumination for illuminating the anterior segment of the eye E. In addition, a dedicated light source may be provided as the anterior-segment illumination.

<Anterior-Segment Observing Optical System>

An observing optical system 90 is provided with the objective lens 10, the dichroic mirror 91, an image forming lens 95, and a two-dimensional photographing device (two-dimensional light receiving device) 97. This observing optical system 90 is arranged for photographing the eye E, to obtain the anterior-segment image. The dichroic mirror 91 has a characteristic of reflecting light with a wavelength emitted from the infrared light source 151, while being transmitted by the other light.

Figure 3:
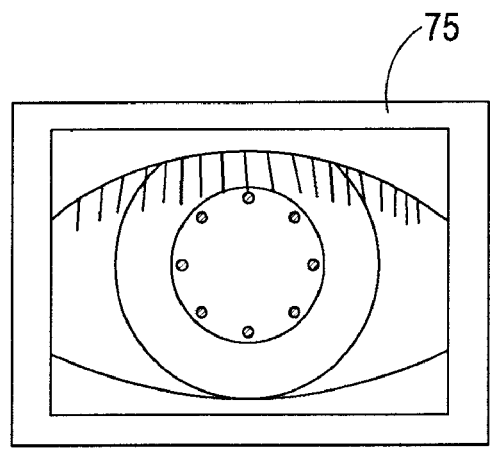
FIG. 3 is a view showing an anterior-segment observation screen shown in a monitor.

The reflected light (including alignment light) obtained by reflection of the light, emitted from the infrared light source 151, on the anterior segment passes through the objective lens 10 and is reflected by the dichroic mirror 91. Thereafter, the light is received by the two-dimensional photographing device 97 via the image forming lens 95. Thereby, the two-dimensional photographing device 97 photographs the anterior-segment image. This anterior-segment image photographed by the photographing device 97 is output to the control part 70, while being displayed on the monitor 75 (refer to FIG. 3).

It is to be noted that the projecting optical system 150 and the observing optical system 90 also serve as a detecting optical system (sensor) for optically detecting the mounted state of the later-mentioned anterior-segment adaptor 500. In addition, the detecting optical system in the present embodiment is configured to detect whether or not the adaptor 500 is mounted, as well as whether or not the adaptor 500 is properly mounted in the inspection window 160.

Next, the adaptor 500 will be described. This adaptor 500 serves to switch the OCT optical system 200 and the SLO optical system 300 from the fundus photographing optical system to the anterior-segment photographing optical system.

Figure 2B:
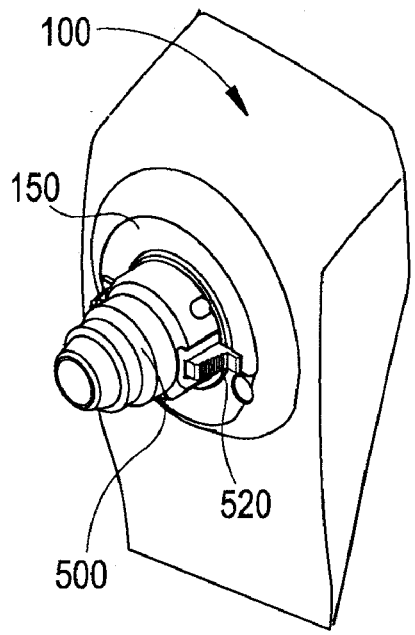

FIG. 2B is a view of the anterior-segment adaptor (hereinafter referred to as adaptor) 500 mounted in the inspection window 160. The adaptor 500 is mounted in the inspection window 160 at the time of photographing the anterior segment. The adaptor 500 has a lens system 510 for moving the focal position of the measurement light on the eye E from the fundus to the anterior segment. This can switch the OCT optical system 200 and the SLO optical system 300 from the fundus photographing optical system to the anterior-segment photographing optical system.

Figure 4:
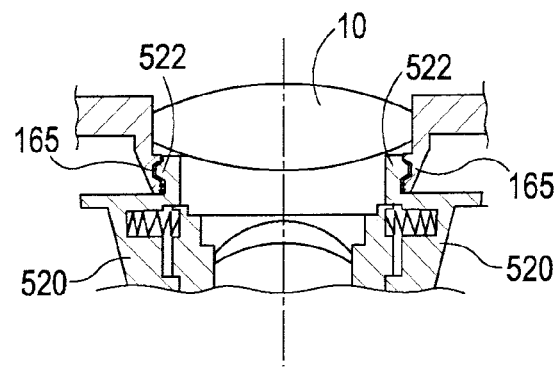
FIG. 4 is a sectional view of the inspection window with the adaptor mounted therein by insertion.

A groove 162 is provided in the inspection window 160. This groove 162 is fitted with a convex part, not shown, of the adaptor 500, thereby to regulate rotation of the adaptor 500 with respect to the inspection window 160. The examiner holds chuck parts 520 provided on the right and left, and mounts the adaptor 500 in the groove 162 so as to fit convex parts 522 of the tips of the chunk parts 520 in concave parts 165 of the inspection window 160 (refer to FIG. 4). It is to be noted that as a mechanism for mounting the adaptor 500 in the inspection window 160, a variety of aspects, such as a mechanism using a screw and a mechanism using a magnet, are considered. In addition, the reason for employing the mechanism as in FIG. 4 in the present embodiment is to allow the adaptor 500 to be smoothly mounted and removed.

Figure 5:
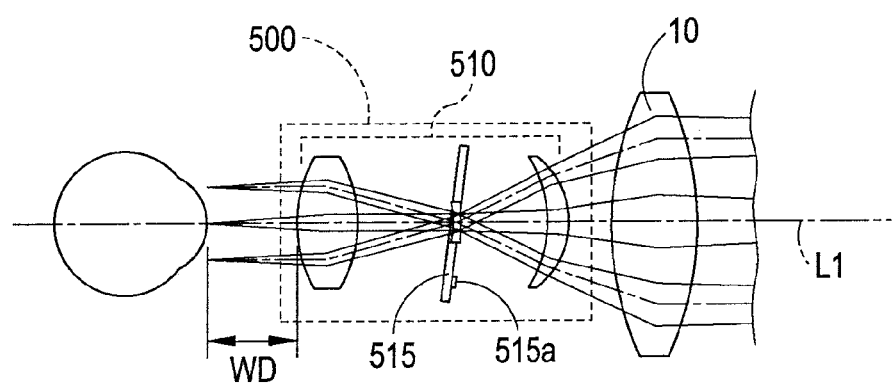
FIG. 5 is an optical side view explaining an internal configuration of the adaptor.
Figure 6:
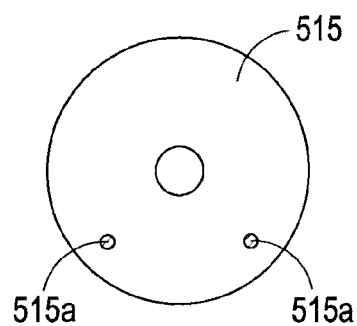
FIG. 6 is a front view showing a flat plate, provided in the adaptor, from the objective lens side.

FIG. 5 is an optical side view explaining an internal configuration of the adaptor 500. The adaptor 500 has a lens system 510 and a flat plate 515. The lens system 510 serves to shift the focal position to the apparatus side so as to be located on the anterior segment. The flat plate 515 is formed with a mirror surface (light reflective member) 515a for detecting the mounted state (refer to front view of FIG. 6).

The lens system 510 is a lens system having a focal distance corresponding to a proper working distance WD between the adaptor 500 and the anterior segment, and is configured to make a main light ray and the optical axis L1 of the measurement light in parallel with each other. The anterior segment is scanned with the measurement light in the transverse direction. The lens system 510 may be made up of one lens, or may be made up of a plurality of lenses.

It is to be noted that in the present embodiment, in the case of photographing the anterior-segment tomographic image, the focusing lens 24 is moved to a predetermined position in a plus-diopter direction (e.g., position of +10D). Thereby, the focal position of the measurement light emitted from the OCT optical system 200 is moved to the apparatus side. That is, mounting of the adaptor 500 and positional adjustment of the focusing lens 24 to the foregoing plus side bring the apparatus into the state of being capable of adjusting the focus of the measurement light on the anterior segment. It is to be noted that at the time of photographing, focusing on the anterior segment is performed after the working distance (front-back distance) of the apparatus to the eye E has been adjusted.

It is to be noted that the control part 70 is connected to the display monitor 75, and controls a display image thereof. Further, the control part 70 is connected with a memory (storing part) 72, an operating part 74 for performing a variety of operations, the scanning driving mechanism 51, the scanning driving mechanism 52, the reference mirror driving mechanism 50, a first driving mechanism 63a for moving the focusing lens 63 in the optical-axis direction, a second driving mechanism 24a for moving the focusing lens 24 in the optical-axis direction, and the like. It is to be noted that as the monitor 75, two monitors, i.e., a monitor for alignment observation and a monitor for photographed image observation, may be used or one shared monitor may naturally be used.

Herein, the control part 70 performs image processing on a light receiving signal output from the light receiving device 83, to form a fundus tomographic image. Further, the control part 70 performs image processing on a light receiving signal output from the light receiving device 68, to form a fundus front image.

In addition, the present apparatus can be set to a fundus photographing mode and an anterior-segment photographing mode. The fundus photographing mode (first photographing mode) is a mode for photographing the tomographic image and the front image of the fundus without using the adaptor 500. On the other hand, the anterior-segment photographing mode (second photographing mode) is a mode for photographing the tomographic image and the front image of the anterior segment with use of the adaptor 500. The control part 70 switches the optical arrangement of the apparatus, the display screen of the monitor, and the like in accordance with the photographing mode.

It is to be noted that in the case of using the adaptor, favorable photographing may not be performed due to insufficient mounting of the adaptor. For example, in the OCT optical system 200, there are cases where quantitative measurement (e.g., cornea thickness measurement, corner measurement) of the anterior-segment tomographic image is performed using the adaptor. In this case, with the adaptor in a slantingly mounted state, the optical axis of the optical system of the apparatus body is shifted from the optical axis of the lens system of the adaptor. This may change the scanning range of the measurement light, to cause an error in a result of the quantitative measurement. Hereinafter, a method for solving the failure in mounting the adaptor will be described.

<Optical Detection of Mounted State of Adaptor 500>

In the ophthalmic photographing apparatus of the present embodiment, at least two among the infrared light sources 151 each serve also as a light source for detection which emits a detection light flux toward the mirror surface 515a. Further, the photographing device 97 also serves as a light receiving device for detection which receives a reflection light flux from the mirror surface 515a. The control part 70 determines the mounted state of the adaptor 500 based on the light receiving signal output from the photographing device 97.

Figure 7:
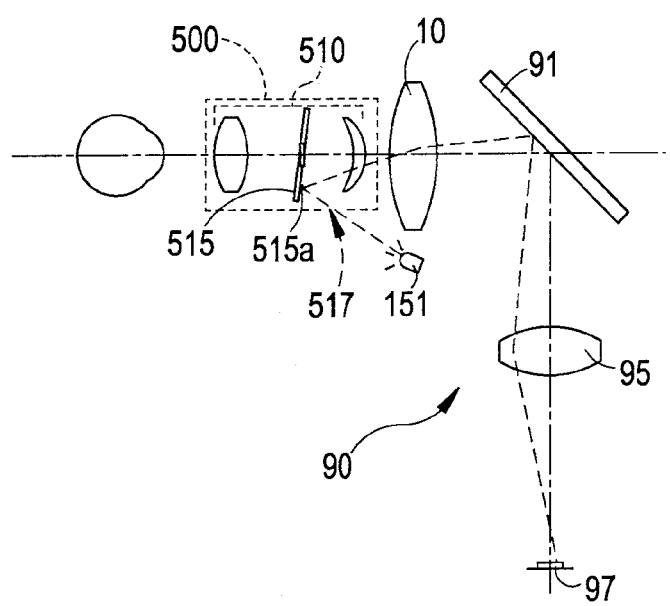
FIG. 7 is a view explaining a function of a mirror surface provided in the adaptor.

FIG. 7 is a view explaining a function of the mirror surface 515a provided in the adaptor 500. In the case of the adaptor 500 being mounted, light emitted from two light sources arranged diagonally downward right and diagonally downward left, among the infrared light sources 151, pass through an opening (hole) 517 formed in the adaptor 500, and are reflected by the two mirror surfaces 515a. The reflected light passes through part of the lens system 510 and the objective lens 10, and is reflected by the dichroic mirror 91. Thereafter, the light is received by the two-dimensional photographing device 97 via the image forming lens 95. This leads to formation of rasters (reflected images) KR and KL (detection signal, mode switching signal) on the photographing device 97 by means of the two mirror surfaces 515a.

Figure 8A:
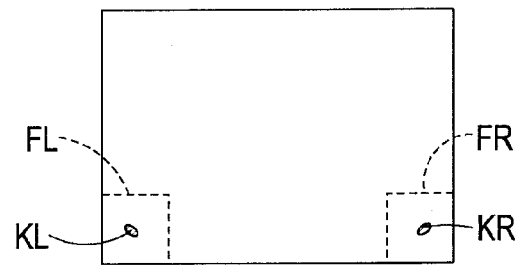
FIGS. 8A, 8B and 8C are views showing a difference in photographed image output from a photographing device in accordance with the mounted states of the adaptor.
Figure 8B:
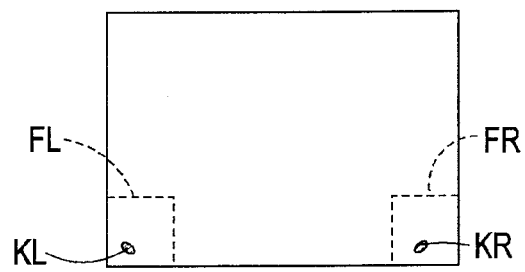
Figure 8C:
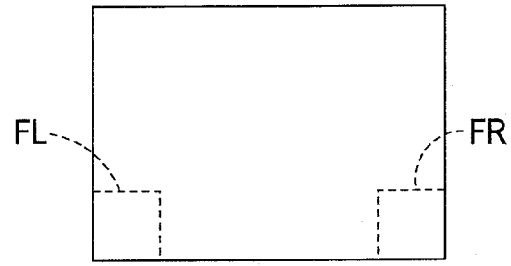

FIGS. 8A, 8B and 8C are views showing a difference in photographed image output from the photographing device 97 in accordance with the mounted states of the adaptor 500. FIG. 8A is a view showing an image obtained when the adaptor 500 is properly mounted. FIG. 8B is a view showing an image obtained when the adaptor 500 is slantingly mounted. FIG. 8C is a view showing an image obtained when the adaptor 500 is not mounted.

Frames (adaptor detection frames) FR and FL formed on the lower right-hand end and lower left-hand end of the photographed image are areas virtually set for determining the mounted state of the adaptor 500.

In the case of the adaptor 500 being properly mounted, as shown in FIG. 8A, the rasters KR and KL are both detected in predetermined positions inside the frames FR and FL. In the case of the adaptor 500 being mounted in a slanted state, the mirror surface 515a is slanted with respect to a proper position. For this reason, as shown in FIG. 8B, at least either the raster KR or KL is detected in a position off the foregoing predetermined position, though inside the frame FR or FL. In the case of the adaptor 500 being not mounted, as shown in FIG. 8C, the rasters KR and KL are both detected in positions off the frames FR and FL (or detected nowhere).

Herein, in the present apparatus, the control part 70 determines mounting/removal of the adaptor 500 based on the photographing signals (detection signal, mode switching signal) output from the photographing device 97, while determining whether or not the adaptor 500 is properly mounted (specifically described later). It is to be noted that as a previous step of this, first, the detected positions of the rasters KR and KL on the photographed image, which have been obtained at the time of the adaptor 500 being properly mounted, are previously stored in the memory 72. Further, positions and sizes of the frames FR and FL are previously set based on the positions of the rasters KR and KL at the time of the adaptor 500 being properly mounted and at the time of the adaptor 500 being not properly mounted. The above steps may be implemented, for example, at the time of calibration of the apparatus.

<Determination of Mounted State>

Figure 9:
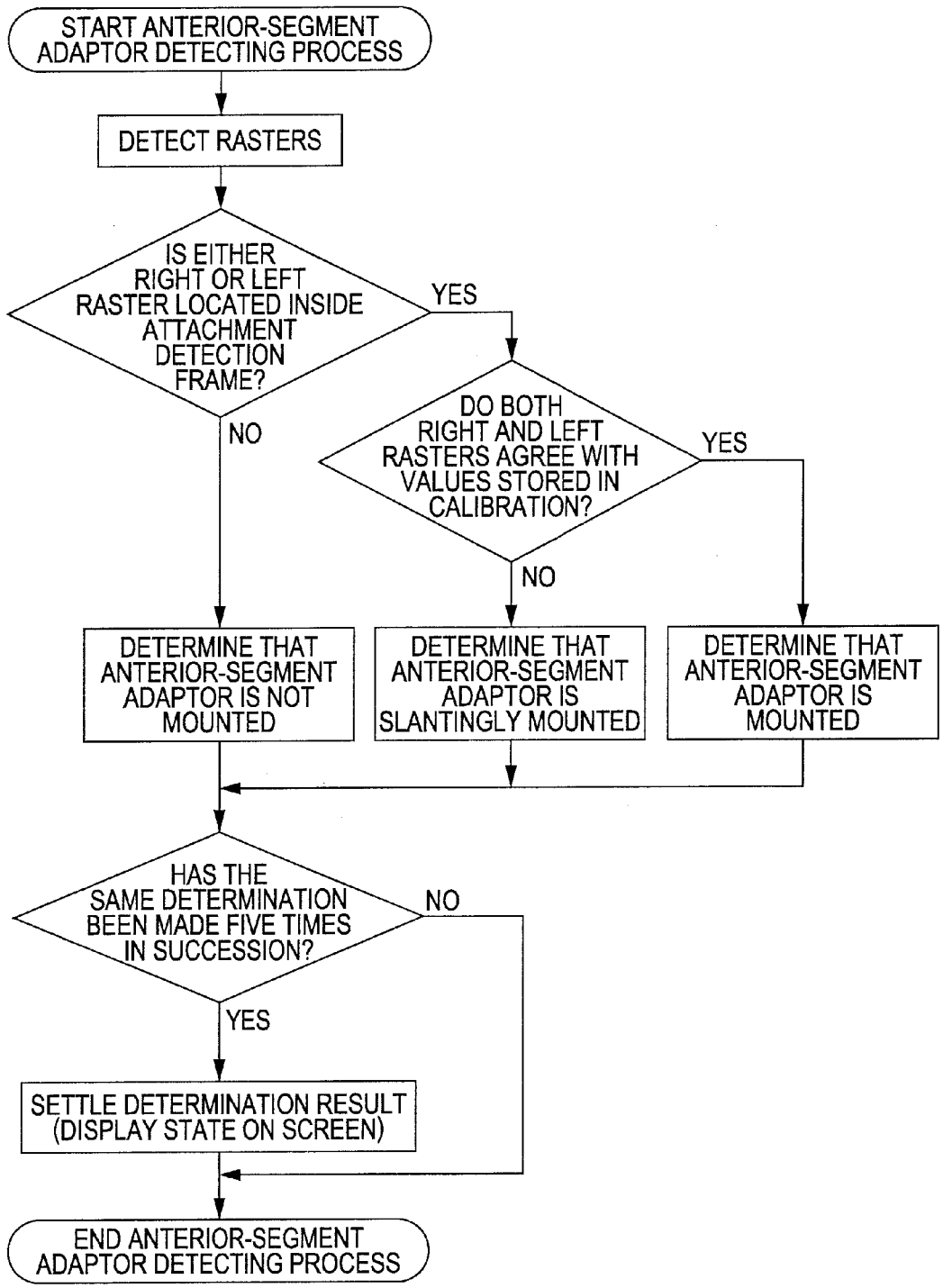
FIG. 9 is a flowchart explaining a technique for detecting the properness of the mounted state.

Hereinafter, a technique for determining the properness of the mounted state will be described using a flowchart of FIG. 9. First, the control part 70 extracts the rasters KR and KL by image processing through use of diameters, luminance levels and the like of the rasters KR and KL. The central positions of the extracted rasters KR and KL are detected.

Next, the control part 70 determines that the adaptor 500 is not mounted when either the raster KR or KL is not inside the frame FR or FL. On the other hand, the control part 70 determines that the adaptor 500 is mounted when either raster is inside the frame FR or FL. When the detected positions of both the rasters KR and KL agree with the positions previously stored in the memory 72, the control part 70 determines that the adaptor 500 is properly mounted. When the positions do not agree, the control part 70 determines that the adaptor 500 is slantingly mounted (improperly mounted).

Herein, the control part 70 successively performs the determination of the mounted state as described above on a photographed image occasionally output from the photographing device 97 at a predetermined frame rate. When the same determination is made five times in succession, that determination result is fixed and displayed on the monitor 75 (determination processing is completed). On the other hand, when the same determination is not obtained five times in succession, the detection processing for the adaptor 500 is stopped without displaying the determination result. In this case, the determination result before the start of the detection processing remains displayed.

Herein, upon settlement of the determination result that the adaptor 500 is not properly mounted, the control part 70 determines that the adaptor 500 is not properly mounted. The control part 70 then displays indication of the adaptor 500 being not properly mounted (or may display indication of the adaptor 500 being slantingly mounted) on the monitor 75. In this case, the examinee mounts the adaptor 500 once again.

On the other hand, upon settlement of the determination result that the adaptor 500 is properly mounted, the control part 70 determines that the adaptor 500 is properly mounted. The control part 70 then switches the photographing mode from the fundus photographing mode to the anterior-segment photographing mode.

It is to be noted that the control part 70 makes determination on the mounted state as thus described in a fixed period (e.g., every one second).

As described above, the properness of the mounted state of the adaptor 500 is detected, and the detection result is notified, thereby to avoid photographing of the anterior-segment image with the adaptor 500 not properly mounted. Further, using the projecting optical system 150 and the observing optical system 90 for the properness detection of the mounted state of the adaptor 500 can eliminate the need for providing a dedicated sensor.

It is to be noted that an installation position and a reflection angle of the mirror surface 515a are preferably set such that the rasters KR and KL at the time of the adaptor 500 being mounted are formed on the ends of the photographing surface of the photographing device 97. This is for preventing erroneous detection of a cornea raster formed by the infrared light source 151 as the rasters KR and KL. On top of this, the sizes of the rasters KR and KL are preferably set so as to be larger than the cornea raster formed by the infrared light source 151. This can avoid the erroneous detection in the image processing. Further, the shape of the mirror surface 515a is not limited to circular, but may be linear, rectangular, or the like.

It is to be noted that at least two or more light sources may be provided for projecting the alignment target to the anterior segment (or illuminating the anterior segment). Further, at least two of those light sources may also serve as the light sources for detection. Moreover, although the mounted state is determined using the two rasters in the foregoing description, three or more rasters may be used.

The configuration for detecting the mounted state of the adaptor 500 is not limited to the one described above. That is, the detection technique for the mounted state of the adaptor 500 is not limited to the optical technique, but may be an electric or magnetic detection technique. For example, a photo sensor, a pressing sensor and the like may be provided in the vicinity (e.g., concave part 165) of the inspection window 160. It is to be noted that in the case of detecting the properness of the mounted state, for example, two pressing sensors may be provided in the vicinity of the inspection window 160. In this configuration, in the case of pressing signals being output from the two pressing sensors, the control part 70 may determine that the mounting is proper. On the other hand, in the case of a pressing signal being output from only one pressing sensor, the control part 70 may determine that the mounting is not proper.

In addition, as the technique for notifying the detection result concerning the properness of the mounted state of the adaptor 500, other than display on the monitor 75, lighting of a dedicated lamp or a voice may also be used.

It is to be noted that in the above description, the control part 70 determines whether or not the mounting of the adaptor 500 in the inspection window 160 is proper. However, the configuration may be formed such that the control part 70 determines mounting/removal of the adaptor 500 that is mounted in the inspection window 160. In this case, for example, the control part 70 determines whether or not the detected positions of both the rasters KR and KL agree with the predetermined positions based on the photographing signals (detection signal, mode switching signal) obtained from the photographing device 97. When determining that these positions agree, the control part 70 determines that the adaptor 500 is mounted. On the other hand, when these positions do not agree, the control part 70 determines that the adaptor 500 is not mounted. The control part 70 then displays the detection result on the monitor 75 while outputting a driving command signal, to change a variety of setting.

Further, in the above configuration, the lens system 510 of the adaptor 500 may be a zooming optical system capable of changing a photographing scaling factor. Moreover, in the case of the mirror surface 515a as described above being provided in the adaptor 500 having the zooming optical system, the detected positions of the rasters KR and KL on the photographing device 97 are moved in accordance with a change in zoom scaling factor. Therefore, the control part 70 may determine whether or not the zoom scaling factor to be changed is proper based on the positions of the rasters KR and KL.

In the above description, the technique for switching the photographing mode has been described, taking as an example the case of using the adaptor for switching from the fundus photographing optical system to the anterior-segment photographing optical system. Naturally, the above technique is also applicable to the case of using the adaptor for switching from the anterior-segment photographing optical system to the fundus photographing optical system. In this case, as the lens system of the adaptor, there is used a lens system for moving the focal position to the examinee side so as to focus on the fundus. It is to be noted that the technique may also be applicable to the fundus camera, in addition to the above fundus photographing apparatus.

Further, the above technique is also applicable to determination of the mounted state or the mounted/removed state of another adaptor mounted in the inspection window of the ophthalmic photographing apparatus. For example, as another adaptors, there can be considered an adaptor for changing a scaling factor which has a lens system for changing a photographing scaling factor of an image of the eye to be photographed, a wide-angle lens adaptor for changing an angle of view of a photographing image, a dioptric adaptor for correcting a dioptric scaling factor of an eye with a severe refractive error, and some other adaptor.

<Automatic Adjustment of Optical Arrangement at the Time of Switching Mode>

Next, an overall operation of the present apparatus will be described. The control part 70 controls driving of the OCT optical system 200 and the SLO optical system 300, to obtain an OCT image or a front image (SLO image). The control part 70 then occasionally updates the OCT image and the front image on the monitor 75 (refer to FIGS. 10 and 11)<

<First Photographing Mode (Fundus Photographing Mode)>

Figure 10:
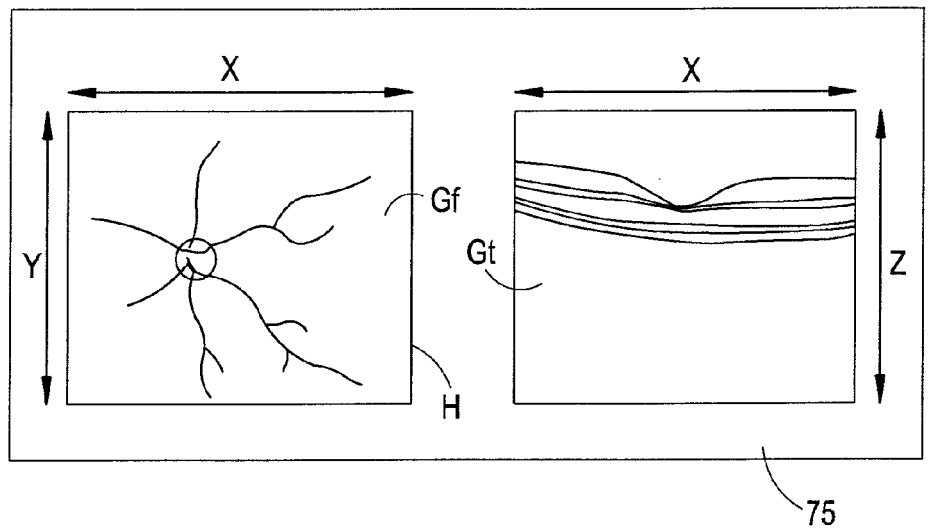
FIG. 10 is a view showing monitors where a fundus front image and a fundus tomographic image are displayed.

First, the first photographing mode will be described. It is to be noted that in the present mode, the adaptor 500 is not used. The examiner directs the examinee to fixedly look at a fixation light, not shown, and then performs alignment on the fundus. When the SLO fundus image is displayed on the monitor 75, the OCT image is obtained by the OCT optical system 200 based on a predetermined scanning pattern. Then, as shown in FIG. 10, the OCT image is displayed on the monitor 75. In this case, the control part 70 controls driving of the driving mechanism 50 based on the light receiving signal output from the light receiving device 83, to adjust the optical-path difference between the measurement light and the reference light such that the fundus tomographic image is obtained. In this case, the reference mirror 31 is moved inside a predetermined movement range corresponding to the difference in ocular axial length of the eye E.

Subsequently, a scanning position/pattern desired by the examiner is set, and a predetermined trigger signal is output. Accordingly, the control part 70 obtains a tomographic image based on the set scanning position/pattern, and stores the obtained image data in the memory 72. Further, at this time, the control part 70 stores a fundus front image obtained by the SLO optical system 300 in the memory 72.

<Second Photographing Mode (Anterior-Segment Photographing Mode)>

Next, the second photographing mode will be described. In the case of executing the second photographing mode, the examiner mounts the adaptor 500 in the inspection window 160. The control part 70 determines the properness of the mounted state of the adaptor 500 as described above. When determining that mounting is proper, the control part 70 switches the photographing mode from the first photographing mode (fundus photographing mode) to the second photographing mode (anterior-segment photographing mode). That is, the control part 70 outputs driving command signals, corresponding to the second photographing mode for controlling driving of the driving mechanism 50, the first driving mechanism 63a and the second driving mechanism 24a, to these mechanisms. Thereby, the driving mechanism 50, the first driving mechanism 63a and the second driving mechanism 24a bring the optical arrangements of the OCT optical system 200 and the SLO optical system 300 to predetermined arrangements corresponding to the second photographing mode. That is, the positions of the respective optical members are automatically adjusted.

<Optical Path Length Adjustment>

In the second photographing mode, the control part 70 further controls driving of the driving mechanism 50 by use of the driving command signal, to locate the reference mirror 31 in the predetermined position corresponding to the second photographing mode. It is to be noted that the control part 70 may prohibit the reference mirror 31 from moving after completion of movement of the reference mirror 31, or may restrict the moving range thereof inside a predetermined range.

It is to be noted that the predetermined position of the foregoing reference mirror 31 is previously stored in the memory 72. Herein, a preferable position of the reference mirror is a position where the anterior-segment tomographic image is obtainable in the state of a working distance between the eye and the apparatus (OCT optical system 200) having been adjusted so as to focus the measurement light to the anterior segment of the eye E.

For example, after adjustment of the working distance, the difference in optical path between the measurement light and the reference light is adjusted such that the anterior-segment tomographic image (refer to cornea C in FIG. 11) is obtained in a position with a predetermined depth. Then, the position of the reference mirror 31 at that time is stored in the memory 72. These positions are obtained by simulation or experiment.

In such a manner as described above, it is possible to avoid obtainment of the anterior-segment tomographic image in the state of the measurement light not being sufficiently focused to the anterior segment of the eye E. It is also possible to avoid erroneous detection of interference light of the reflected light from the lens system 510 of the adaptor 500 and the reference light at the time of automatically adjusting the optical path length.

It is to be noted that, concerning movement of the position of the reference mirror 31, it is preferable to provide a sensor (encoder, potentiometer, or the like) for detecting the position of the reference mirror 31. In this case, the control part 70 moves the reference mirror 31 to the predetermined position stored in the memory 72 based on a detection signal from this sensor. Further, a sensor (e.g., photo sensor) may be provided in a position corresponding to the predetermined position inside the movement range of the reference mirror 31. When the sensor detects that the reference mirror 31 has been located in the predetermined position, the control part 70 stops movement of the reference mirror 31.

It is to be noted that in the above description, the optical path length of the reference light is changed for adjusting the optical-path difference between the measurement light and the reference light. However, this is not restrictive, and the optical path length of the measurement light may be changed. For example, the collimator lens 22 and the end of the optical fiber 39b may be moved in the optical-axis direction.

In addition, the foregoing predetermined position of the reference mirror 31 may be set to a position where obtainment of the tomographic image of the lens system 510 can be avoided. The tomographic image of the lens system 510 is obtained by the interference light of the reflected light, obtained by reflection of the measurement light on the lens system 510, and the reference light. In this case, the position of the reference mirror 31 where the tomographic image of the lens system 510 is obtained is previously obtained, and the movement range of the reference mirror 31 may be set as a predetermined position so as to avoid the previously obtained position.

In this case, when switching the photographing mode to the second photographing mode, the control part 70 outputs a driving command signal to the driving mechanism 50, thereby to move the reference mirror 31 within a movement range set for avoiding obtainment of the tomographic image of the lens system 510. After obtainment of the tomographic image, the control part 70 stops movement of the reference mirror 31.

<Focus Adjustment>

Concerning the OCT optical system 200, the control part 70 controls driving of the second driving mechanism 24a, to locate the focusing lens 24 in the predetermined position corresponding to the second photographing mode. When the focusing lens 24 reaches the predetermined position, the control part 70 stops and prohibits driving of the second driving mechanism 24a.

It is to be noted that the predetermined position of the focusing lens 24 is previously stored in the memory 72. A preferable position of the focusing lens 24 is a position where the measurement light can be focused to the anterior segment in a set predetermined proper working distance, as well as a position where the main light ray of the measurement light toward the anterior segment is in parallel with the optical axis L1. That position is preferably stored in the memory 72 as the predetermined position of the focusing lens 24. These positions are obtained by simulation or experiment. It is to be noted that as a technique for locating the focusing lens 24 in the predetermined position, a similar technique to the one for the reference mirror 31 may be used.

Further, concerning the SLO optical system 300, the control part 70 controls driving of the first driving mechanism 63a, and moves the focusing lens 63 to the predetermined position corresponding to the second photographing mode in a similar manner to the OCT optical system 200. It is to be noted that the technique for setting the movement position of the focusing lens 63 is similar to the case of the OCT optical system 200 above, and the description thereof is thus omitted.

Further, at the time of switching to the second photographing mode, the control part 70 controls the display of the monitor 75, thereby to change the display content from the one for fundus photographing to the one for anterior-segment photographing.

Subsequently, the control part 70 selectably displays respective scanning patterns for anterior-segment photographing (e.g., cornea line scan, cornea cross scan, and corner line scan), prepared in plurality in accordance with photographed regions. Further, the control part 70 switches the display unit of the scanning range from an angle-of-view unit (e.g., 40°) to a distance unit (e.g., 6.0 mm). Moreover, the control part 70 makes a display indicating prohibition of the movement of the respective focusing lenses 24 and 63, while prohibiting driving of the first driving mechanism 63a and the second driving mechanism 24a, to actually prohibit movement of each of the lenses. This can fix the positions of the lenses 24 and 63 to the predetermined positions.

Furthermore, after directing the examinee to fixedly look at the fixation light, not shown, the examiner performs alignment on the anterior segment. Herein, the examiner moves the apparatus housing 100 in the front-back direction so as to be focused on the front image on the monitor 75 while looking at the front image on the monitor 75, thereby adjusting the working distance of the apparatus housing 100 to the eye. It is to be noted that the examiner may adjust the working distance so that the OCT image can be displayed with accuracy.

It is to be noted that in some cases, it may be necessary, for focus to the anterior segment, to ensure the working distance between the apparatus and the eye E (e.g., a case where a measure such as increasing a thickness of a forehead rest provided in the apparatus has been taken). In this case, an electric-powered driving part for moving the housing 100 with electric power may be provided. In this case, the control part 70 may control driving of the electric-powered driving part by a driving command signal, to move the housing 100 toward the predetermined front-back direction corresponding to the anterior-segment photographing.

Figure 11:
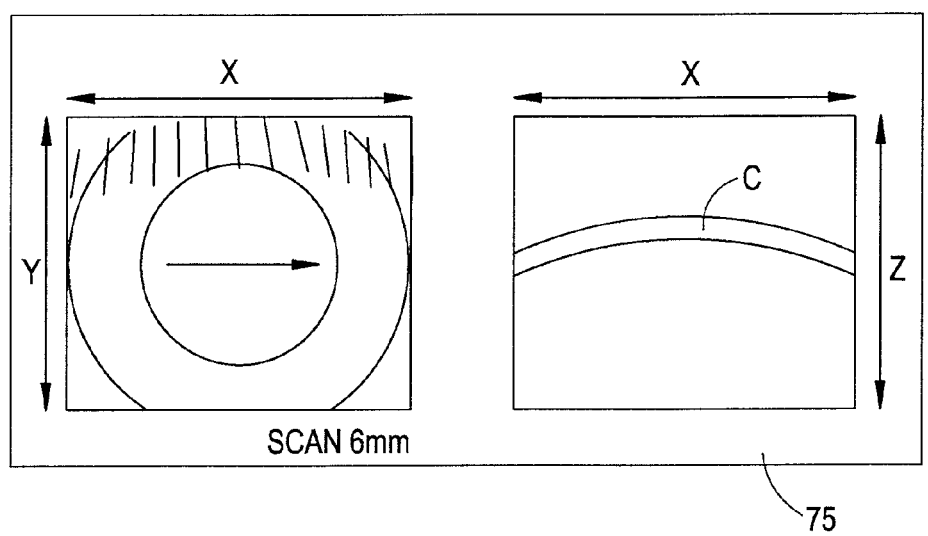
FIG. 11 is a view showing monitors where an anterior-segment front image and an anterior-segment tomographic image are displayed.

Upon completion of the alignment on the anterior segment in such a manner as described above, the anterior-segment tomographic image is obtained by the OCT optical system 200 based on the previously set scanning pattern. The obtained anterior-segment tomographic image is displayed as a moving image on the monitor 75 (FIG. 11).

Subsequently, the examiner sets a desired scanning position/pattern, and further outputs a predetermined trigger signal. In accordance with this, the control part 70 obtains the anterior-segment tomographic image while controlling driving of the scanning driving mechanism 51 based on the set scanning position/pattern. The control part 70 then stores the obtained image date in the memory 72. At this time, the control part 70 also stores in the memory 72 the anterior-segment front image obtained by the SLO optical system 300.

As described above, the control part 70 changes setting of each member based on a determination result concerning the mounted/removed state of the adaptor 500, so as correspond to the second photographing mode. This allows the anterior segment to be smoothly photographed.

It is to be noted that the control part 70 preferably discriminates between the tomographic image photographed in the first photographing mode as the fundus image and the tomographic image photographed in the second photographing mode as the anterior-segment image, and makes the discrimination result correspond to the tomographic images and stored in the memory 72.

In addition, when the adaptor 500 is removed from the apparatus after photographing of the anterior segment as described above, both the rasters KR and KL detected in the predetermined positions disappear from the photographed surface of the photographing device 97. In this case, in the determination of the mounted state of the adaptor 500, both the rasters KR and KL detected in the predetermined positions disappear from the inside of the frames FR and FL. For this reason, the control part 70 determines that the adaptor 500 is not mounted (i.e., the control part 70 determines that the adaptor 500 has been removed from the inspection window 160). In accordance with this, the control part 70 switches the photographing mode from the anterior-segment photographing mode to the fundus photographing mode.

In the case of switching the photographing mode to the first photographing mode, the control part 70 outputs driving command signals, corresponding to the first photographing mode for controlling driving of the driving mechanism 50, the first driving mechanism 63a and the second driving mechanism 24a, to these mechanisms. Thereby, the driving mechanism 50, the first driving mechanism 63a and the second driving mechanism 24a bring the optical arrangements of the OCT optical system 200 and the SLO optical system 300 to arrangements corresponding to the first photographing mode. That is, the positions of the respective optical members are automatically adjusted. With this adjustment, the reference mirror 31 and the respective focusing lenses 24 and 63 are moved to predetermined original point positions.

Further, the control part 70 controls the display of the monitor 75, so as to change the display content from the one for anterior-segment photographing to the one for fundus photographing.

More specifically, the control part 70 selectably displays scanning patterns for fundus photographing which are prepared in plurality (e.g., line scan, cross scan, and radial scan). Further, the control part 70 switches the display unit of the scanning range from a distance unit (e.g., 6.0 mm) to an angle-of-view unit (e.g., 40°). Moreover, the control part 70 makes a display indicating permission of movement of the respective focusing lenses 24 and 63, while actually permitting movement of each of the lenses.

It is to be noted that in the above description, the control part 70 controls changes corresponding to the second photographing mode based on the detection signal (photographing signal output from the photographing device 97) which is emitted upon mounting of the adaptor 500. However, this is not restrictive, and for example, after receipt of the detection signal, the control part 70 may display on the monitor 75 a message urging switching to the second photographing mode (e.g., asking a YES/NO question as to whether or not to switch to the second photographing mode). In this case, the examiner may output a predetermined selection signal concerning switching of the photographing mode (mode switching signal) to the control part 70 via the operating part 74. The control part 70 may then perform the foregoing change control based on the input signal.

Further, in the above description, the control part 70 executes the process of switching the photographing mode from the first photographing mode to the second photographing mode in accordance with mounting detection of the adaptor 500. However, this is not restrictive, and for example, the control part 70 may switch the photographing mode based on the mode switching signal input via the operating part 74 (predetermined mode change-over switch).

Moreover, in the above description, the optical arrangements of both the OCT optical system 200 and the SLO optical system 300 are changed (adjusted) at the time of switching the photographing mode. However, this is not restrictive, and the control part 70 may be set so as to adjust the optical arrangement of either the OCT optical system 200 or the SLO optical system 300 at the time of switching the photographing mode.

It is to be noted that in the above description, the control part 70 outputs the driving command signal while switching the photographing mode, to adjust the optical arrangements of the OCT optical system 200 and the SLO optical system 300. However, this is not restrictive, and the control part 70 may adjust the optical arrangement by use of the driving command signal at the time of actual photographing in the second photographing mode. For example, after switching to the second photographing mode, the control part 70 may output the driving command signal based on an operation signal input via the operating part 74, to start adjustment of the optical arrangement. Further, the ophthalmic photographing apparatus of the present embodiment may be provided with an alignment detection optical system for detecting the working distance of the apparatus to the eye. In this case, the control part 70 determines whether or not the above working distance has reached a proper working distance based on the detection signal of the alignment detection optical system. When determining that the working distance has reached the proper working distance, the control part 70 may then perform automatic adjustment of the reference mirror 31 for obtaining the tomographic image.

Further, the foregoing automatic adjustment of the optical arrangement at the time of switching the mode is applicable not only to an apparatus that is mounted with the adaptor 500 so as to obtain the tomographic images of the fundus and the anterior segment, but also to an apparatus having a configuration to switch the focal position of the measurement light between the anterior segment and the fundus by insertion/removal of the lens system inside the apparatus.

Further, the control part 70 may emit the mode switching signal for switching the photographing mode from the fundus photographing mode to the anterior-segment photographing mode when detecting that the adaptor 500 is properly mounted. Herein, the control part 70 may switch the optical arrangement of the apparatus, the display screen of the monitor and the like in accordance with the anterior-segment photographing mode.

In this case, upon settlement of the determination result that the adaptor 500 is not properly mounted, the control part 70 may output the detection signal with indication of the adaptor 500 being not properly mounted. Herein, based on that detection signal, the control part 70 displays indication of the adaptor 500 being not properly mounted (or may display indication of the adaptor 500 being slantingly mounted) on the monitor 75.

Moreover, upon settlement of the determination result that the adaptor 500 is properly mounted, the control part 70 may output the detection signal with indication of the adaptor 500 being properly mounted. Herein, based on the detection signal, the control part 70 may emit the mode switching signal for switching the photographing mode from the fundus photographing mode to the anterior-segment photographing mode.

Furthermore, the ophthalmic photographing apparatus according to an aspect of the present invention can be expressed as follows: an ophthalmic photographing apparatus including: an interference optical system (200) including: a measurement light source (27); and a splitter (26) that splits light emitted from the measurement light source, such that the split lights travel in a measurement optical path for guiding part of the light to the eye as measurement light and in a reference optical path for generating reference light, the interference optical system synthesizing reflected light from the measurement optical path, which is obtained by reflection of the measurement light on the eye, with the reference light from the reference optical path, to guide the synthesized light to a detector (83); a first driving part (50) that moves an optical member arranged in the measurement optical path or the reference optical path in an optical-axis direction in order to adjust an optical-path difference between the measurement optical path and the reference optical path; an image obtaining part (70) that is connected to the detector and obtains tomographic images of a fundus and an anterior segment based on signals output from the detector; a mode switching unit (70, 74) that emits a switching signal for switching a photographing mode from a first photographing mode for photographing the tomographic image of the fundus to a second photographing mode for photographing the tomographic image of the anterior segment; and a driving control unit (70) that controls driving of the first driving part based on a driving command signal in the case of photographing in the second photographing mode, to locate the optical member in a predetermined position corresponding to the second photographing mode.

The ophthalmic photographing apparatus according to an aspect of the present invention can also be expressed as follows: an ophthalmic photographing apparatus for photographing a tomographic image of an eye using interference light, which is obtained by interference of a plurality of lights including measurement light reflected on an examinee's eye and having different optical path lengths, including: an optical member that moves on an optical path of any of the lights to adjust an optical-path difference among the plurality of lights; and a control part that arranges the optical member in a position corresponding to either a first photographing mode for photographing a tomographic image of a fundus or a second photographing mode for photographing a tomographic image of an anterior segment.

While the invention has been illustrated and described in detail, the foregoing description is in all aspects illustrative and not restrictive. It is therefore understood that numerous modifications and variations can be devised without departing from the spirit and scope of the invention.

What is claimed is:

1. An ophthalmic photographing apparatus for photographing a tomographic image of an eye, comprising:
    an interference optical system including:
        a measurement light source; and
        a splitter that splits light emitted from the measurement light source, such that the split lights travel in a measurement optical path for guiding part of the light to the eye as measurement light and in a reference optical path for generating reference light,
        the interference optical system synthesizing reflected light from the measurement optical path, which is obtained by reflection of the measurement light on the eye, with the reference light from the reference optical path, to guide the synthesized light to a detector;
    a first driving part that moves an optical member arranged in one of the measurement optical path and the reference optical path in an optical-axis direction in order to adjust an optical-path difference between the measurement optical path and the reference optical path;
    an image obtaining part that is connected to the detector and obtains a tomographic image of a fundus in a fundus photographing mode and a tomographic image of an anterior segment in an anterior segment photographing mode based on a light receiving signal output from the detector; and
    a driving control unit that controls driving of the first driving part in the case of the fundus photographing mode and driving of the first driving part to locate the optical member in a predetermined position corresponding to the anterior segment photographing mode in the case of the anterior segment photographing mode.

2. The ophthalmic photographing apparatus according to claim 1, wherein the predetermined position is a position where the anterior-segment tomographic image is obtainable by the image obtaining part in the state that a distance between the eye and the apparatus has been adjusted so as to focus the measurement light to the anterior segment.

3. The ophthalmic photographing apparatus according to claim 1, further comprising:
    a second driving part that moves, in the optical-axis direction, a focusing lens arranged in the measurement optical path for adjusting a focus on the fundus,
    wherein in the case of photographing in the anterior segment photographing mode, the driving control unit controls driving of the second driving part to locate the focusing lens in a predetermined position corresponding to the anterior segment photographing mode.

4. The ophthalmic photographing apparatus according to claim 1, wherein the interference optical system is one of a spectral domain OCT optical system and a swept source OCT optical system.

5. The ophthalmic photographing apparatus according to claim 1, wherein the interference optical system comprises an optical scanner that is arranged in the measurement optical path and scans the eye with the measurement light.

6. The ophthalmic photographing apparatus according to claim 1, further comprising:
   an inspection window that can be mounted with an adaptor having a lens system for moving a focal position of the measurement light from the fundus to the anterior segment.

7. The ophthalmic photographing apparatus according to claim 6, wherein the predetermined position is a position where it is possible to avoid obtainment of a tomographic image of the lens system by light obtained by synthesizing the reflected light, which is obtained by reflection of the measurement light on the lens system, with the reference light.

8. The ophthalmic photographing apparatus according to claim 6, further comprising:
   a sensor for detecting a mounted state of the adaptor in the inspection window; and
   an alarm that notifies a result of detection made by the sensor.

9. The ophthalmic photographing apparatus according to claim 8, wherein the sensor detects whether or not the adaptor is properly mounted in the inspection window.

10. The ophthalmic photographing apparatus according to claim 8, wherein
    the adaptor is provided with an optical reflector,
    the sensor has a detection light source that emits detection light toward the optical reflector, and a detection light receiving device that receives reflected light from the optical reflector, and
    the mounted state of the adaptor is detected based on a light receiving signal output from the detection light receiving device.

11. The ophthalmic photographing apparatus according to claim 10, further comprising:
    an anterior-segment observing optical system that has a two-dimensional light receiving device for observing an anterior-segment image of an examinee's eye,
    wherein the two-dimensional light receiving device in the anterior-segment observing optical system also serves as the detection light receiving device.

12. The ophthalmic photographing apparatus according to claim 11, further comprising:
    an anterior-segment light source for projecting an alignment target to the anterior segment or illuminating the anterior segment,
    wherein the anterior-segment light source also serves as the detection light source.

13. The ophthalmic photographing apparatus according to claim 11, wherein the sensor detects a reflected image obtained by reflection of the detection light on the optical reflector based on the light receiving signal output from the two-dimensional light receiving device, and determines whether or not the adaptor is properly mounted based on whether or not a position of the detected reflected image is a predetermined position.

14. The ophthalmic photographing apparatus according to claim 8, wherein the driving control unit switches the photographing mode from the fundus photographing mode to the anterior segment photographing mode based on a detection signal output from the sensor.

* * * * *